United States Patent [19]

Schnegg et al.

[11] Patent Number: 4,918,195

[45] Date of Patent: Apr. 17, 1990

[54] PROCESS FOR PREPARING TRIAZOLES FUSED WITH AROMATIC SYSTEMS BY REACTION OF O-ARYLENEDIAMINES WITH NITRITES

[75] Inventors: Ulrich Schnegg, Leverkusen; Ulrich Bormann, Langerwehe, both of Fed. Rep. of Germany

[73] Assignee: Bayer Aktiengesellschaft, Leverkusen, Fed. Rep. of Germany

[21] Appl. No.: 243,384

[22] Filed: Sep. 12, 1988

[30] Foreign Application Priority Data

Sep. 24, 1987 [DE]  Fed. Rep. of Germany ....... 3732169

[51] Int. Cl.$^4$ ............................................. C07D 249/18
[52] U.S. Cl. ...................................................... 548/257
[58] Field of Search ............... 548/257, 260, 261, 259; 203/38, 36

[56] References Cited

U.S. PATENT DOCUMENTS

| 3,564,001 | 2/1971 | Long .................................... 548/257 |
| 3,637,514 | 1/1972 | Spatz et al. ........................ 548/257 |
| 3,639,431 | 2/1972 | McTeer ............................... 548/257 |
| 4,158,660 | 6/1979 | Gavin et al. . |
| 4,170,521 | 10/1979 | Carr . |
| 4,299,965 | 11/1981 | Chan et al. . |
| 4,363,914 | 12/1982 | Long et al. ........................ 548/257 |
| 4,424,360 | 1/1984 | Hagedorn ......................... 548/257 |

FOREIGN PATENT DOCUMENTS

| 0062864 | 10/1982 | European Pat. Off. . |
| 2822506 | 12/1978 | Fed. Rep. of Germany . |
| 1451409 | 10/1976 | United Kingdom ................ 548/259 |

OTHER PUBLICATIONS

*Chemical Abstracts,* vol. 95, No. 9, Aug. 31, 1981, pp. 789-790.

*Primary Examiner*—Donald G. Daus
*Attorney, Agent, or Firm*—Sprung Horn Kramer & Woods

[57] ABSTRACT

Triazoles fused with aromatic systems are prepared by reaction of o-arylenediamines with nitrites and subsequent purification by distillation, the distillation being carried out in the presence of an alkaline substance.

23 Claims, No Drawings

PROCESS FOR PREPARING TRIAZOLES FUSED WITH AROMATIC SYSTEMS BY REACTION OF O-ARYLENEDIAMINES WITH NITRITES

BACKGROUND OF THE INVENTION

1. Field of the Invention

The present invention relates to a process for preparing triazoles fused with aromatic systems by reaction of o-arylenediamines with nitrites and subsequent purification by distillation.

Triazoles fused with aromatic systems are valuable corrosion inhibitors, in particular for copper surfaces, but they can also be used as intermediates for numerous syntheses.

2. Description of the Related Art

It is already known to react o-phenylenediamine and o-diaminotoluenes in excess acetic acid with sodium nitrite (DE-OS (German Published Specification) No. 2,351,595, equivalent to U.S. Pat. Nos. 3,970,667; 3,732,239; 3,564,001). It is further known to use a lower alkyl ester of nitrous acid instead of sodium nitrite (DE-OS German Published Specification) No. 2,822,506); in this case, the reaction is carried out in an aprotic solvent, such as a hydrocarbon, or in a protic solvent, such as an alcohol or ether alcohol which can also contain small amounts of water. To initiate the diazotization and the amount of an acid, for example of a carboxylic acid, is ring closure reaction to give the triazole, a catalytic required. Instead of using a carboxylic acid as reaction initiator, the prior art reveals that acidic benzotriazole or tolytriazole have also been used (EP Nos. 62,864; 75,459).

Particular attention has always been given to the purification of the fused triazole obtained. Thus, in the process of abovementioned DE-OS (German Published Specification) No. 2,351,595, the reaction mixture, without intermediate isolation of the triazole, is made alkaline using aqueous sodium hydroxide solution and subjected several times of clarifying filtration; after the mixture has been acidified again using nitric acid, the precipitated triazole is isolated as such. In DE-OS (German Published Specification) No. 2,822,506, the reaction mixture, after distilling off volatile components, is inoculated and the triazole is recovered by crystallization. U.S. Pat. No. 3,732,239 shows that, if crude diaminotoluene is used before starting the diazotization and ring closure reaction, an expensive purification by distillation is necessary. After the reaction with aqueous sodium nitrite, the tolyltriazole is extracted from the reaction mixture which contains water and acetic acid using chloroform. After the chloroform has been distilled off, the tolyltriazole is recrystallized, for example from benzene.

However, it has also been attempted, after the diazotization with sodium nitride in a water/acetic acid reaction medium, first to separate off the benzotriazole as an oil, to wash it with water and finally to distil the benzotriazole itself under reduced pressure. Since this simple vacuum distillation was evidently not completely satisfactory, the purification of benzotriazole was refined by vacuum distillation in the presence of small amounts of formaldehyde (U.S. Pat. No. 4,170,521).

The purification by distillation apparently did not give sufficient purity and colour stability of the fused triazoles so that EP No. 75,459 additionally shows, evidently to avoid an unsatisfactory distillation, another process in which alkyl nitrites are reacted in $C_6$–$C_{10}$ alkanols as the reaction medium and the triazole obtained is extracted from this reaction medium by means of aqueous sodium hydroxide solution.

SUMMARY OF THE INVENTION

Surprisingly, it has now been found that, despite the unsatisfactory prior art results, a purification of fused triazoles by distillation can be achieved if the distillation is carried out in the presence of an alkaline substance.

The invention therefore relates to a process for preparing triazoles fused with aromatic systems by reaction of crude or purified o-arylenediamines with nitrites and subsequent purification by distillation, characterized in that the distillation of the fused triazole is carried out in the presence of an alkaline substance.

DETAILED DESCRIPTION OF THE INVENTION

Suitable alkaline substances are, for example, non-volatile alkali (ne earth) metal compounds. These are alkaline compounds of lithium, sodium, potassium, rubidium, caesium, magnesium, calcium, strontium or barium, preferably alkaline compounds of sodium, potassium, calcium or magnesium, particularly preferably alkaline sodium or calcium compounds and very particularly preferably alkaline sodium compounds.

Examples of such compounds which may be mentioned are the hydroxides, oxides, carbonates, bicarbonates and salts of other weak acids. Preference is given to the carbonates, hydroxides and oxides of alkali (ne earth) metals, preference is given to the hydroxides or oxides and particular preference is given to the hydroxides.

These alkaline compounds can be added to the fused triazole to be purified before it enters the distillation apparatus, or they can also be introduced into the distillation apparatus simultaneously with the triazole to be purified, either together therewith or separately therefrom. The alkaline compound can be used as such or in solution, for example, in aqueous solution. A preferred dosage form is that of the water-soluble hydroxides of alkali (ne earth) metals in the form of an aqueous solution. These aqueous solutions have, for example, a concentration of 2–70% by weight, preferably 10–60% by weight, particularly preferably 30–55% by weight of hydroxide, based on the entire aqueous solution.

The amount of alkaline substance used is 0.01–20% by weight, preferably 0.05–10% by weight, particularly preferably 0.1–1% by weight, based on the weight of the fused triazole.

o-Arylenediamines can be, for example, o-phenylenediamine, o-naphthylenediamine or o-pyridylenediamine, preferably o-phenylenediamine. These o-arylenediamines can be monosubstituted or polysubstituted by lower alkyl, for example 1–4 C atoms such as methyl, ethyl, propyl, isopropyl, butyl or isobutyl, by halogen such as fluorine, chlorine or bromine, by nitro, by lower alkoxy, for example having 1–4 C atoms such as methoxy, ethoxy, propoxy or butoxy. Of the substituents mentioned, 1–3, preferably 1–2, particularly preferably 1 substituent can be present on the o-arylenediamine. In addition, the unsubstituted o-arylenediamine is preferred. Particularly preferred examples which may be mentioned are o-phenylenediamine, nitrophenylenediamine, hydroxyphenylenediamine, chlorophenylenediamine, 2,3-diaminotoluene and 3,4-diaminotoluene.

These o-arylenediamines can be used not only in pure but also in crude form, such as they are formed in industrial processes.

Nitrites which can be used are alkali metal nitrite, for example sodium nitrite, or lower alkyl esters of nitrous acid, preferably alkyl esters of nitrous acid. These alkyl esters have, for example, 1–6 C atoms, preferably 1–2 C atoms, particularly preferably 1 C atom; examples are methyl nitrite, ethyl nitrite, propyl nitrite, isopropyl nitrite, butyl nitrite, isobutyl nitrite, amyl nitrite, isoamyl nitrite and hexyl nitrite. The reaction medium can be an aqueous acid medium, for example including acetic acid, propionic acid or butyric acid, mineral acids or it can be an organic medium consisting of hydrocarbons or alcohols or ether alcohols. Preferably, an organic solvents, particularly preferably, an alcohol is used as the reaction medium. These alcohols can have 1–6 C atoms, preferably 1–3 C atoms, particularly preferably 1 C atom, such as methanol, ethanol, propanol, isopropanol, butanol, isobutanol, amyl alcohol or hexanol. Preferably, the combination of using a $C_1$–$C_6$-alkyl nitrite, preferably a $C_1$–$C_2$-alkyl nitrite, particularly preferably methyl nitrite, with a $C_1$–$C_6$-alkanol, preferably $C_1$–$C_3$-alkanol, preferably methanol, is employed.

If complete conversion is the goal, the amount of nitrite employed is in general 1–1.2 moles, preferably 1.0–1.1 moles, per mole of o-arylenediamine.

In the case where an alkali metal nitrite is used, the reaction is generally carried out in the presence of an acid, for example in the presence of acetic acid or mineral acids. In the case where an alkyl nitrite is used, the reaction can be carried out in the presence of an acid, for example acetic acid or mineral acids; however, instead of acetic acid, the fused triazole to be prepared can also be used as the acidic initiator for the diazotization and ring closure reaction. In the case where an alkyl nitrite is used in an alcoholic solvent, the preferred variation of the process according to the invention is, however, that any acidic initiator, such as of the type mentioned, can be omitted.

The process according to the invention is generally carried out at a temperature from −20° to +100° C., preferably from 20°–80° C. The general variation is to carry out the process at atmospheric pressure. However, it can also be carried out at increased or reduced pressure.

The process according to the invention can be carried out batchwise and also continuously. In a preferred variation of the process, the preparation of the fused triazoles is carried out continuously, for example in a bubble column apparatus. The amount of alcoholic reaction medium used is about 50–200 ml of alkanol per 100 g of o-arylenediamine. If an alkyl nitrite is the preferred reagent, it is, in the case of methyl nitrite, prepared, for example, in a methyl nitrite generator from sodium nitrite, methanol and sulphuric acid and used in the preferred reaction in a one- or multi-stage bubble column apparatus in approximately equimolar amounts (a slight molar excess within the above context being possible). In the case of a batchwise reaction, gaseous methyl nitrite is in general introduced into the alcoholic solution of the o-arylenediamine until saturation.

The workup of a reaction mixture which has been obtained, for example, by using an alcoholic solvent and an alkyl nitrite is in general carried out by distilling off the alcoholic solvent, if desired together with the water which may have been used, and introducing the residue of such a first distillation together with an alkaline substance or after addition of such a substance to the crude fused triazole into a suitable further distillation apparatus, for example a thin-film evaporator or a falling-film evaporator. To obtain uniform wetting of the heat transfer surface of such a distillation apparatus, a polymeric or oligomeric wax such as high molecular weight polydiols or paraffins, which can be recovered as undistillable residue, can be added to the crude fused triazole.

The fused triazole preparable according to the invention retains it clear, often slightly yellowish colour over a long period, whereas fused triazoles which have been obtained by a prior art process rapidly discolour and lose the gloss of the freshly distilled material. A particular advantage of the process according to the invention is that, in general, crude, particularly low-priced diamines give a stable colour and an end product of high purity.

EXAMPLE 1

Benzotriazole (for comparison)

108 g of freshly distilled 99.8% pure o-phenylenediamine were suspended in 125 ml of methanol and heated to 50° C. At this temperature, gaseous methyl nitrite, prepared from sodium nitrite solution (25% strength), methanol and sulphuric acid (48% strength), was introduced. The rate of addition was such that no off-gas left the reaction flask. As soon as the reaction mixture did not absorb any more gas (about 2 hours), a sample was removed and tested for complete conversion. This was followed by first distilling off methanol and then water from the reaction mixture. With the addition of polywax (polydiol 1550) as a lubricant, the mixture was then distilled continuously through a thin-film evaporator at 4 mbar and a heater temperature of 220° C. Benzotriazole came over at about 165° C. and 4 mbar. Such freshly distilled benzotriazole is 99.9% pure, as analyzed by gas chromatography. It has a slightly yellow colour. On standing for several weeks, the pale yellow colour fades to a palate beige colour.

EXAMPLE 2

Benzotriazole

The example was carried out in the same way as Example 1. However, instead of freshly distilled very pure o-phenylenediamine, crude o-phenylenediamine having a content of 98.8% (residue: p-phenylenediamine, aniline, chloroanilines and unknowns) was used and reacted with methyl nitrite as described. After distilling off methanol, about 1% by weight of 50% strength sodium hydroxide solution, based on crude benzotriazole, was added. The distillation was then carried out as in Example 1. The benzotriazole obtained (99.9% pure was pale yellow. Even after standing for a month, the clear colour was fully preserved.

EXAMPLE 3

Benzotriazole (for comparison)

Example 2 was repeated, but no sodium hydroxide solution was added. The freshly distilled benzotriazole (99.9% pure) was pale yellow but changed colour within a few days to weeks via beige to greyish green.

EXAMPLE 4

Tolyltriazole 244 g of crude o-toluylenediamine (isomeric mixture consisting of 2,3- and 3,4-diaminotoluene) were dissolved in 210 ml of methanol and reacted at 50° C. as in Example 1 with methyl nitrite. After the addition of about 1% by weight of 50% strength sodium hydroxide solution, the mixture was distilled as in Example 1. The column head temperature was about 175° C. at 4 mbar. The distilled tolyltriazole was 99.7% pure. The colour was pale yellow and remained unchanged for months.

EXAMPLE 5

Tolyltriazole

A continuously operated bubble column was charged at the base of the bubble column (80 mm in diameter) with a mixture consisting of 6 parts of o-toluylenediamine and 4 parts of methanol (containing about 10% of water) at a rate of 10 kg/h. Also at the base of the bubble column, about 3.0 kg/h of gaseous methyl nitrite, prepared from methanol, sodium nitrite solution and aqueous sulphuric acid in a continuously operated gas generator, was introduced through a ring nozzle. The off-gas from the bubble column was purified by passing it through a scrubber containing o-toluylenediamine in methanol. The reaction mixture from the scrubber can be introduced into the bubble column. After the reaction mixture had left the bubble column, methanol was first introduced off continuously, then after adding about 1% by weight of sodium hydroxide solution (50% strength), water and finally the tolyltriazole formed were distilled off from the reaction mixture. The product was pale yellow and stable in colour.

What is claimed is:

1. A process for preparing triazoles fused with aromatic systems comprising reacting o-arylenediamines with nitrites and subsequently conducting purification by distillation, wherein the distillation of the fused triazole is carried out in the presence of an alkaline substance consisting essentially of hydroxides, oxides, carbonates, bicarbonates of a compound selected from the group consisting of lithium, sodium, potassium, calcium, strontium, barium, rubidium, cesium or magnesium.

2. A process according to claim 1, wherein the compound is a sodium, potassium, calcium, or magnesium compound.

3. A process according to claim 2, wherein the compound is a sodium or calcium compound.

4. A process according to claim 2, wherein the compound is a sodium compound.

5. A process according to claim 1, wherein the alkaline substance is a hydroxide or oxide.

6. A process according to claim 5 wherein the alkaline substance is a hydroxide.

7. A process according to claim 5, wherein the hydroxide is a water-soluble hydroxide in the form of an aqueous solution.

8. A process according to claim 7, characterized in that a 2–70% by weight aqueous solution of the hydroxide is used.

9. A process according to claim 8, characterized in that a 10–60% by weight aqueous solution of the hydroxide is used.

10. A process according to claim 9, characterized in that a 30–35% by weight aqueous solution of the hydroxide is used.

11. A process according to claim 1, characterized in that 0.1–20% by weight of the alkaline substance, based on the weight of the fused triazole, are used.

12. A process according to claim 11, characterized in that 0.2–10% by weight of the alkaline substance, based on the weight of the fused triazole, are used.

13. A process according to claim 12, characterized in that 0.3–5% by weight of the alkaline substance, based on the weight of the fused triazole, are used.

14. A process according to claim 1, wherein the o-arylenediamine is o-phenylenediamine or o-toluylenediamine.

15. A process according to claim 1, characterized in that the nitrite used is a $C_1$–$C_6$-alkyl nitrite and the reaction is carried out in a $C_1$–$C_6$-alkanol as the reaction medium.

16. A process according to claim 15, characterized in that a $C_1$–$C_6$-alkyl nitrite is used.

17. A process according to claim 16, characterized in that methyl nitrite is used.

18. A process according to claim 1, characterized in that the reacting is initiated in the absence of an acidic compound.

19. A process according to claim 1, characterized in that the reaction is carried out continuously.

20. A process according to claim 19, characterized in that the reaction is carried out continuously in a bubble column apparatus.

21. A process according to claim 1, wherein the triazole fused with an aromatic system is benzotriazole or tolyltriazole.

22. A process according to claim 1, which further comprising conducting the reacting in the presence of an acid.

23. A process according to claim 22, wherein the acid is acetic acid or mineral acid.

* * * * *